| United States Patent [19] | [11] Patent Number: 4,806,352 |
|---|---|
| Cantrell | [45] Date of Patent: * Feb. 21, 1989 |

[54] IMMUNOLOGICAL LIPID EMULSION ADJUVANT

[75] Inventor: John L. Cantrell, Corvallis, Mont.

[73] Assignee: Ribi ImmunoChem Research Inc., Hamilton, Mont.

[*] Notice: The portion of the term of this patent subsequent to Feb. 7, 2006 has been disclaimed.

[21] Appl. No.: 852,120

[22] Filed: Apr. 15, 1986

[51] Int. Cl.$^4$ ................................................ A61K 39/00
[52] U.S. Cl. ........................................ 424/92; 424/89; 424/88; 514/21; 514/885; 514/937
[58] Field of Search ............... 424/88, 92; 514/885, 514/937, 938, 939, 943

[56] References Cited

U.S. PATENT DOCUMENTS

| | | | |
|---|---|---|---|
| 3,993,775 | 11/1976 | Williams | 514/885 |
| 4,036,953 | 7/1977 | Adam et al. | 514/2 X |
| 4,185,090 | 1/1980 | McIntire | 514/885 X |
| 4,307,229 | 12/1981 | Liar et al. | 514/924 X |
| 4,338,334 | 7/1982 | Jensen | 514/825 X |
| 4,436,727 | 3/1984 | Ribi et al. | 424/177 |
| 4,436,728 | 3/1984 | Ribi et al. | 424/177 |
| 4,606,918 | 8/1986 | Allison | 514/8 X |

OTHER PUBLICATIONS

Reynolds et al., "Infection and Immunity", vol. 28, No. 3, pp. 937–943: 1980.

American Journal of Veterinary Research, vol. 44, No. 1, pp. 72–75: 1983.

B. E. Straw et al., Can J. Comp. Med.: 1985; 49, pp. 149–151.

M. Brugh et al., American Journal of Veterinary Research, vol. 44, No. 1: 1983.

Primary Examiner—Matthew A. Thexton
Assistant Examiner—Catherine S. Kilby
Attorney, Agent, or Firm—Burgess, Ryan & Wayne

[57] ABSTRACT

An immunological adjuvant is provided which enhances the immune response against antigens, and accordingly is useful in vaccines. The adjuvant system is comprised of (1) a lipid emulsion system containing a metabolizable oil, a low molecular weight polyol and lecithin and (2) at least one refined detoxified bacterial biological adjuvant.

20 Claims, No Drawings

IMMUNOLOGICAL LIPID EMULSION ADJUVANT

FIELD OF THE INVENTION

This invention relates in general to an immunological adjuvant. In one aspect, this invention is directed to an immunological adjuvant system which enhances the immune response against antigens, and hence is useful in vaccines. In a further aspect, the present invention relates to an immunological adjuvant system containing a lipid emulsion system combined with a biological adjuvant and antigen. The invention also relates to a method of preparing the immunological adjuvant and its use in enhancing the immune response against antigens.

BACKGROUND OF THE INVENTION

Prior to the present invention, a variety of adjuvants have been reported in the literature to potentiate the immune response to numerous antigens and particularly, the immune response to vaccines. It is known that the Freund complete or incomplete adjuvants are considered the classic adjuvants to which most other adjuvants are compared. However, their reactogenicity precludes the clinical use of such adjuvants in animals or humans. Other materials, such as mineral oil and aluminum hydroxide, have also been used as adjuvants, but they invariably suffer from disadvantages. For example, oil is known to produce tissue irritation, and aluminum hydroxide may enhance antibody responses only minimally. Moreover, many of the adjuvants currently available contain components which are not metabolizable in humans, and accordingly, this greatly limits their use. Additionally, most adjuvants in use today, are difficult to prepare in that they may require time consuming procedures and the use, in some cases, of elaborate and expensive equipment to formulate a vaccine and adjuvant system.

More recently, as reported by Reynolds et al. in Infection and Immunity, Volume 28, No. 3, pages 937-943, 1980, some adjuvant activity of a metabolizable lipid emulsion was found with inactivated viral vaccines. It is indicated in this study that this lipid emulsion adjuvant significantly enhances the immune responses of several warm blooded species to inactivated viral antigens. It is also indicated that this lipid emulsion, which is comprised of highly refined peanut oil emulsified in aqueous vaccines with glycerol and lecithin, has advantages over other oil-based adjuvants. For example, the lipid components of the emulsion are metabolizable by normal host constituents if employed in humans or animals, are easily emulsified by gentle agitation, and are relatively non-reactogenic.

In the American Journal of Veterinary Research, Volume 44, No. 1, pages 72-75, 1983, a comparison of inactivated viral vaccines containing different emulsion adjuvants is set forth. It is indicated in this article that the immunization studies revealed marked differences in the effectiveness of mineral oil adjuvants and the lipid emulsion adjuvant as described in the Reynolds et al. reference.

However, while the literature discloses the use of a metabolizable lipid emulsion as an adjuvant, prior to the present invention, there has been no indication of the use of a metabolizable lipid emulsion with other components which would further potentiate an immune response.

SUMMARY OF THE INVENTION

In its broad aspect, the present invention is directed to an immunological adjuvant, a process for its preparation and its use in potentiating the immune response to antigens.

DETAILED DISCUSSION OF THE INVENTION

As indicated above, the present invention is directed to a novel immunological adjuvant, its preparation and use.

The novel immunological adjuvant of the present invention is comprised of:

1. A lipid emulsion system (LES) containing:
   (a) metabolizable oil,
   (b) a low molecular weight polyol,
   (c) lecithin, and
2. A refined detoxified bacterial biological adjuvant, which may be, but is not limited to refined detoxified endotoxin (RDE), trehalose dimycolate (TDM), protein from *Salmonella typhimurium* (STM), and the like.

It has been found that the immunological adjuvant of the present invention greatly enhances the immune response against a wide variety of both natural and synthetic antigens, including viral, bacterial, fungal, or protozoan antigens. The only requirement of the antigen which is employed in the immunological adjuvant system of the present invention is that it be capable of eliciting an immune response in a host and that the response will be enhanced by the adjuvant of this invention with which it is combined.

The adjuvant of the present invention is also useful for enhancing the immune response against antigens which are genetically engineered proteins as well as antigens which are in vitro synthesized peptides. These may include, but are not limited to, antigens related to polio virus, influenza virus, AIDS-related viruses, hepatitis viruses, herpes viruses, cytomegalo-viruses, foot and mouth disease virus, feline leukemia virus, rabies virus, infectious bovine rhinotracheitis virus, bovine diarrhea virus, Newcastle disease virus, fowl hepatitis, hog cholera virus, pseudo rabies virus, malarial peptides, etc. The adjuvant system of the present invention is also useful with natural proteins such as toxoids from diptheria, tetanus, enterotoxogenic coli, and pertussis bacteria.

The immune responses to polysaccharide vaccines such as those derived from the capsules of pneumococci, meningococci, *Hemophilus influenzae*, or fungi, or polysaccharides from the cell walls of both gram positive or gram negative bacteria are enhanced by the adjuvant system.

Also, vaccines composed of inactivated whole viruses, bacteria, fungi, or protozoans have greater immunological potency in this adjuvant system. These may include the agents cited above and also mycobacteria, clostridia, enteric bacilli, vaccinia virus and the like.

It has been found that the adjuvants of the present invention containing both the lipid emulsion system and a suitable refined bacterial adjuvant, as indicated above, are found to be more effective in adjuvantizing antigens than either component alone. In fact, the use of both components provides an enhanced effect which appears to be greater than the sum total of the effects of the separate components.

Moreover, the lipid emulsion employed in the immunological adjuvants of the present invention is characterized by being metabolizable and hence exhibits desirable properties not found in the conventional adjuvants such as mineral oil. As previously indicated, it is known that the non-metabolizable adjuvants, such as mineral oil, induce a granulomatous response in animals and therefore cannot be used in the treatment of humans. Additionally, it has also been observed that the cost of preparing a composition, such as a vaccine, containing an antigen and the immunological adjuvant of the present invention is markedly less than the water-in-oil emulsions of the prior art. Since less time is needed to prepare the adjuvant systems of the present invention, additional savings are also made.

As indicated above, the first component of the immunological adjuvant of this invention is a lipid emulsion system (LES) containing a metabolizable oil, a low molecular weight polyol, such as glycerin, and lecithin. In practice, it has been found that the metabolizable oil is preferably a fatty oil comprised mainly of diglycerides and triglycerides of oleic and linoleic acids. Particularly preferred are the fatty vegetable oils such as those contained in, or obtained from, peanut oil, sunflower seed oil, safflower seed oil, corn oil and the like. Other oils such as olive oil, cottonseed oil or squalene can also be employed in the adjuvants of the present invention. Thus, the main criteria is that the oil be metabolizable, compatible with the other components of the emulsion system and adjuvant itself, and be effective in combination with the other components in enhancing the immune response against antigens.

In practice, a wide variety of polyols can be utilized in the lipid emulsion system. The polyols employed are low molecular weight polyols which are liquid, miscible with the metabolizable oil, and in which the lecithin component is soluble. Suitable polyols include, among others, ethylene glycol, 1, 2 — propane diol, 1, 3 — propane diol, glycerin, 1, 4 — butane diol, 1,3 — butane diol, 1, 2, 4 — butane triol, 1, 5 — pentane diol and the like.

As indicated, the third component of the lipid emulsion system is lecithin. The term "lecithin" as used throughout the specification and appended claims is intended to encompass any of a group of phospholipids having the general formula:

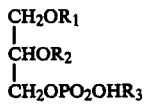

wherein $R_1$ and $R_2$ are fatty acids containing up to 22 carbon atoms and $R_3$ is choline. These phospholipids are usually a mixture of the diglycerides of stearic, palmitic, linoleic or linolenic fatty acids linked to the choline ester of phosphoric acid.

The three components of the lipid emulsion system, that is the metabolizable oil, polyol and lecithin, are known materials and are commercially available. The three components employed in the lipid emulsion system are, of course, highly refined and of a pharmaceutically acceptable grade.

In practice it has been found that the lipid emulsion system should preferably contain from about 30 to about 60 weight percent of the metabolizable oil, from about 30 to about 60 weight percent of a low molecular weight polyol, and from about 1 to about 15 weight percent lecithin.

To illustrate the preparation of the lipid emulsion system, one part (10 grams) of sterile lecithin is dissolved in 10 parts (100 grams) of white glycerin by gentle heating at 60° C. on a hot plate while stirring with a magnetic bar. Prior to use, the glycerin is sterilized by passing it through a 0.2 micrometer filter unit. Thereafter the glycerin and lecithin mixture is placed in a sterile blender cup and 10 parts (100 grams) of peanut oil, which is also sterilized by means of a 0.2 micrometer filter, is slowly added to the glycerin and lecithin mixture while blending at a moderate speed.

The second component of the immunological adjuvant is a refined detoxified bacterial adjuvant. Particularly preferred is refined detoxified endotoxin, hereinafter also referred to as RDE, which is obtained from Re mutant strains of Salmonella. The detoxified endotoxin can also be obtained from other enterobacteriaciae as disclosed in U.S. Pat. No. 4,436,728 which is incorporated herein by reference. The detoxified endotoxin can also be prepared synthetically and by genetic engineering techniques. Other refined detoxified bacterial adjuvants can also be employed, either alone or in combination with RDE and include, but are not limited to, trehalose dimycolate (TDM), protein from *Salmonella typhimurium* (STM), and the like.

In the preparation of the immunological adjuvant system of this invention, the antigen and the second component are prepared separately by adding the antigen in sterile saline to the refined detoxified endotoxin also in sterile saline and wherein the concentration of antigen is from about 1 to about 1000 micrograms per 0.2 milliliter and the concentration of endotoxin is from about 25 to about 200 micrograms per 0.2 milliliter.

The immunological adjuvants of the present invention, containing the lipid emulsion system and the biological adjuvant and antigen, are conveniently prepared by first blending the metabolizable oil, polyol and lecithin to form the lipid emulsion system. The refined detoxified endotoxin, as indicated above, is separately prepared in sterile saline to which is added the antigen also in sterile saline. Thereafter, the sterile saline containing the antigen and refined detoxified endotoxin is added to the lipid emulsion system and the mixture blended in a vortex machine or a blender until an emulsion is obtained.

In practice, three volumes of the antigen-RDE solution is added to one volume of the lipid emulsion system and the combination mixed as indicated to obtain a white milky solution (emulsion). Blending of the two components to obtain the emulsion is usually accomplished in from 2 to 5 minutes.

Although the optimum ratio of the two components of the immunological adjuvant is three volumes of the antigen-RDE saline solution to one volume of the lipid emulsion system, the ratio of the antigen-RDE mixture to the lipid emulsion system can vary from about 1 to 1 to about 8 to 1 with about a 3 to 1 ratio being preferred.

By the above process, an emulsion is obtained of the aqueous antigen solution which results in a slow release of the antigen, a prolongation of antigenic stimulation, and a cellular stimulation close to the antigen which is induced by the detoxified bacterial adjuvants. This combination of activities enhances the host's response to the antigen, as is evident from Table 1 in the examples.

As indicated above, the immunological adjuvants of the present invention in admixture with a variety of antigens enhance the immune response against such antigens and hence are useful in vaccines for both veterinary and human hosts.

The adjuvant of the present invention is useful for enhancing the immune response against antigens which are genetically engineered proteins as well as antigens which are in vitro synthesized peptides. These may include, but are not limited to, antigens related to polio virus, influenza virus, AIDS-related viruses, hepatitis viruses, herpes viruses, cytomegalo-viruses, foot and mouth disease virus, feline leukemia virus, rabies virus, infectious bovine rhinotracheitis virus, bovine diarrhea virus, Newcastle disease virus, fowl hepatitis, hog cholera virus, pseudo rabies virus, malarial peptides, etc. The adjuvant system of the present invention is also useful with natural proteins such as toxoids from diptheria, tetanus, enterotoxogenic coli, and pertussis bacteria.

The immune responses to polysaccharide vaccines such as those derived from the capsules of pneumococci, meningococci, *Hemophilus influenzae,* or fungi or from the cell walls of both gram positive or gram negative bacteria are enhanced by the adjuvant system.

Also, vaccines composed of inactivated whole viruses, bacteria, fungi, or protozoans have greater immunological potency in this adjuvant system. These may include the agents cited above and also mycobacteria, clostridia, enteric bacilli, vaccinia virus, etc.

In practice it has been found that the refined detoxified endotoxin is used in a concentration of from about 25 to about 200 micrograms per dose with a particularly enhanced immune response being elicited at approximately 100 micrograms per dose. If desired, other components or additives can be employed in conjunction with the adjuvants of the present inventions.

The following examples are illustrative of the invention.

EXAMPLE 1

The antibody response of mice immunized with a foot and mouth disease viral peptide (FMD) alone, and with the immunological adjuvants of the present invention was determined. BALB/C mice 6 to 8 weeks of age were given a single subcutaneous injection (0.2 ml) of foot and mouth disease virus synthetic peptide (FMD). The dose administered was 200 μg/mouse. In other injections, FMD was combined with RDE and/or LES. RDE was administered at a dose of 100 μg. LES was mixed with the aqueous FMD solution at a 1:1 V/V ratio. The mixture was vortexed for about 2 minutes at room temperature. Mice were bled by the retro-orbital sinus at various times after inoculation.

The results obtained are set forth in Table I below:

TABLE 1

Antibody response of BALB/C mice immunized with FMD viral peptide combined with RDE-LES lipid emulsion.

| Material Injected | Reciprocal of EIA Titers (IgG) (Days after Immunization) | | | | | |
|---|---|---|---|---|---|---|
| | 7 | 14 | 21 | 40 | 60 | 73 |
| FMD** | 50 | 50 | 200 | 100 | 100 | 100 |
| FMD + LES | 50 | 50 | 200 | 200 | 400 | 200 |
| FMD + RDE + LES (100 μg) | 800 | 1600 | 6400 | 25600 | 25600 | 6400 |
| FMD + RDE + LES (50 μg) | 100 | 400 | 400 | 3200 | 3200 | 1600 |

**The foot and mouth disease peptide (FMD) was obtained from Dr. J. Bittle of Scripps Clinic and Research Foundation, La Jolla, CA. It was synthesized by scientists at Scripps and was designated FMD peptide 65; it was coupled to tetanus toxoid before use.

It is evident from the data obtained that the use of the two component immunological adjuvants provide unexpected and surprising enhancement of the immune response with marked prolongation of antigenic stimulation. In particular when a 100 μg dose of RDE was employed, even markedly higher immune responses were observed.

EXAMPLE 2

In this experiment, BALB/C mice (6 mice/group) were given a subcutaneous injection (0.2 ml/animal) of the following: Group 1, 100 μg dextran in saline; Group 2, 100 μg dextran+50 μg RDE in saline; Group 3, 100 μg dextran+50 μg RDE emulsified in an equal volume of LES, Group 4, 100 μg dextran emulsified in a vial containing a lyophilized emulsion of 50 μg RDE+50 μg trehalose dimycolate (TDM) dose; Group 5 received no antigen.

On day 20 after primary immunization, all mice in each group received a second injection that was prepared the same way as the first injection.

Individual serum samples were collected by serial bleedings at various times after immunization.

The results obtained are set forth below in Table II:

TABLE II

Passive hemagglutinin (HA) titers of sera from mice immunized with Dextran antigen alone or in combination with MPL adjuvant in various types of solutions.

| Group | Treatment | Reciprocal of HA Titers (Days After Immunization) | | | |
|---|---|---|---|---|---|
| | | 6 | 16 | 30 | 48 |
| 1 | Dextran | 163(15)* | 340(33) | 672(54) | 240(60) |
| 2 | Dextran + RDE | 800(50) | 1228(126) | 2368(248) | 1386(168) |
| 3 | Dextran + RDE + LES | 928(76) | 2668(660) | 3200(400) | 2816(232) |
| 4 | Dextran + RDE + TDM | 373(10) | 1120(88) | 1813(173) | 1493(163) |
| 5 | None | 20(10) | 40(20) | 20(10) | 10(10) |

*Results are expressed as the average reciprocal titer for each group. Starting dilution for each serum sample was 1:10. Numbers in parenthesis are the average titers of serums treated with 0.1 M 2-mercaptoethanol, and represent the response attributable to IgG antibody.

What is claimed is:

1. An immunological adjuvant useful for enhancing the immune response against antigens, in a host, comprised of:
 (1) a lipid emulsion system containing,
  (a) a metabolizable oil,
  (b) a low molecular weight polyol,
  (c) lecithin, and
 (2) a refined, detoxified bacterial adjuvant.

2. The adjuvant of claim 1 wherein said metabolizable oil is a fatty oil comprised mainly of the diglycerides and triglycerides of oleic and linoleic acids.

3. The adjuvant of claim 1 wherein said metabolizable oil is selected from the group consisting of vegetable oils and animal oils.

4. The adjuvant of claim 3 wherein said vegetable oil is selected from the group consisting of peanut oil, sunflower seed oil and safflower seed oil.

5. The adjuvant of claim 3 wherein said animal oil is squalene.

6. The adjuvant of claim 1 wherein said lipid emulsion system is comprised of from about 30 to about 60 percent by weight of metabolizable oil; from about 30 to 60 percent by weight of a polyol, and from about 1 to about 15 percent by weight of lecithin.

7. An adjuvant system combining the immunological adjuvant of claim 1 with an antigen.

8. The adjuvant system of claim 7 wherein said antigen and said refined detoxified bacterial adjuvant are contained in a sterile saline solution.

9. The adjuvant of claim 8 wherein the concentration of antigen in said sterile saline solution is from about 5 to about 5000 µg/ml and the concentration of refined detoxified bacterial adjuvant in said sterile saline solution is from about 125 to 1000 µg/ml.

10. The adjuvant of claim 7 wherein said lipid emulsion system is comprised of a sterile saline solution of from about 30 to about 60 percent by weight of metabolizable oil; from about 30 to 60 percent by weight of a polyol, and from about 1 to about 15 percent by weight of lecithin, and the concentration of antigen in said sterile saline solution is from about 5 to about 5000 µg/ml and the concentration of refined detoxified bacterial adjuvant in said sterile saline solution is from about 125 to 1000 µg/ml.

11. The adjuvant of claim 7 wherein said refined detoxified bacterial adjuvant is selected from the group consisting of refined detoxified endotoxin, trehalose dimycolate or protein from *Salmonella typhimurium*.

12. The adjuvant of claim 7 wherein said refined detoxified bacterial adjuvant is refined detoxified endotoxin.

13. A method of enhancing the immune response in a host against an antigen which is capable of eliciting an immune response in said host, which comprises administering to said host an immune response enhancing amount of the immunological adjuvant system of claim 7.

14. A method of enhancing the immune response in a host against an antigen which is capable of eliciting an immune response in said host, which comprises administering to said host an immune response enhancing amount of the immunological adjuvant system of claim 10.

15. The method of claim 13 wherein the immunological adjuvant system is administered by a single injection containing from about 25 to about 200 µg of refined detoxified bacterial adjuvant per dose.

16. The method of claim 13 wherein said antigen is a genetically engineered protein.

17. The method of claim 13 wherein said antigen is an in vitro synthesized peptide.

18. The method of claim 13 wherein said antigen is a hepten conjugated with a carrier molecule.

19. The method of claim 13 wherein said antigen is a naturally occurring protein.

20. The method of claim 13 wherein said antigen is an inactivated preparation of virus, bacteria, fungi, or protozoa.

* * * * *